(12) United States Patent
Dorogusker et al.

(10) Patent No.: US 8,047,966 B2
(45) Date of Patent: Nov. 1, 2011

(54) INTERFACING PORTABLE MEDIA DEVICES AND SPORTS EQUIPMENT

(75) Inventors: Jesse Dorogusker, Los Altos, CA (US); Scott Krueger, San Francisco, CA (US); Lawrence Bolton, Fremont, CA (US); Emily C. Schubert, San Jose, CA (US); Gregory T. Lydon, Santa Cruz, CA (US); Debbie Lambert, San Francisco, CA (US); Michael Hailey, Campbell, CA (US); Donald Ginsburg, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 12/238,436

(22) Filed: Sep. 26, 2008

(65) Prior Publication Data

US 2009/0221404 A1 Sep. 3, 2009

Related U.S. Application Data

(60) Provisional application No. 61/032,805, filed on Feb. 29, 2008.

(51) Int. Cl.
   *A63B 71/00* (2006.01)
(52) U.S. Cl. ............................................. 482/9; 482/1
(58) Field of Classification Search ................... 482/1, 4, 482/8, 9, 51, 901, 902
   See application file for complete search history.

(56) References Cited

U.S. PATENT DOCUMENTS

| | | | |
|---|---|---|---|
| 4,673,861 A | 6/1987 | Dubovsky et al. | |
| 4,850,899 A | 7/1989 | Maynard | |
| 4,924,216 A | 5/1990 | Leung | |
| 4,938,483 A | 7/1990 | Yavetz | |
| 5,150,031 A | 9/1992 | James et al. | |
| 5,186,646 A | 2/1993 | Pederson | |
| 5,213,555 A * | 5/1993 | Hood et al. | 482/57 |
| 5,277,624 A | 1/1994 | Champion | |
| 5,314,391 A * | 5/1994 | Potash et al. | 482/7 |
| 5,466,200 A * | 11/1995 | Ulrich et al. | 482/4 |
| 5,471,128 A | 11/1995 | Patino et al. | |
| 5,525,981 A | 6/1996 | Abernethy | |

(Continued)

FOREIGN PATENT DOCUMENTS

EP    1104150 A2    5/2001

(Continued)

OTHER PUBLICATIONS

Altec Lansing, "inMotion Users Guide," Corp. Headquarters, 535 Rte.6 & 209, Milford, PA 18337.

(Continued)

*Primary Examiner* — Loan Thanh
*Assistant Examiner* — Sundhara M Ganesan
(74) *Attorney, Agent, or Firm* — Kilpatrick Townsend & Stockton LLP

(57) ABSTRACT

Circuits, methods, and apparatus that allow sports or other equipment, such as gym or other cardio equipment, to write data to a media player. Examples further provide the uploading of this data to a computer and third-party website. To monitor progress, the third-party website can be used to track workout data over time. The third party-website can also collect data from other users, which is particularly useful for providing a competitive environment. This data can then be graphically displayed in various ways to provide encouragement.

13 Claims, 15 Drawing Sheets

U.S. PATENT DOCUMENTS

| | | | |
|---|---|---|---|
| 5,591,104 A * | 1/1997 | Andrus et al. | 482/7 |
| 5,592,588 A | 1/1997 | Reekes et al. | |
| 5,618,045 A | 4/1997 | Kagan et al. | |
| 5,648,712 A | 7/1997 | Hahn | |
| 5,702,323 A * | 12/1997 | Poulton | 482/8 |
| 5,727,866 A | 3/1998 | Kraines et al. | |
| 5,732,361 A | 3/1998 | Liu | |
| 5,754,027 A | 5/1998 | Oglesbee et al. | |
| 5,835,862 A | 11/1998 | Nykanen et al. | |
| 5,845,217 A | 12/1998 | Lindell et al. | |
| 5,888,172 A * | 3/1999 | Andrus et al. | 482/7 |
| 5,890,995 A * | 4/1999 | Bobick et al. | 482/4 |
| 5,964,847 A | 10/1999 | Booth, III et al. | |
| 6,012,105 A | 1/2000 | Rubbmark et al. | |
| 6,050,924 A * | 4/2000 | Shea | 482/57 |
| 6,078,402 A | 6/2000 | Fischer et al. | |
| 6,078,789 A | 6/2000 | Bodenmann et al. | |
| 6,125,455 A | 9/2000 | Yeo | |
| 6,130,518 A | 10/2000 | Gabehart et al. | |
| 6,152,856 A * | 11/2000 | Studor et al. | 482/8 |
| 6,154,798 A | 11/2000 | Lin et al. | |
| 6,161,027 A | 12/2000 | Poirel | |
| 6,169,387 B1 | 1/2001 | Kaib | |
| 6,175,358 B1 | 1/2001 | Scott-Jackson et al. | |
| 6,178,514 B1 | 1/2001 | Wood | |
| 6,184,652 B1 | 2/2001 | Yang | |
| 6,184,655 B1 | 2/2001 | Malackowski | |
| 6,211,649 B1 | 4/2001 | Matsuda | |
| 6,230,205 B1 | 5/2001 | Garrity et al. | |
| 6,252,380 B1 | 6/2001 | Koenck | |
| 6,268,845 B1 | 7/2001 | Pariza et al. | |
| 6,271,605 B1 | 8/2001 | Carkner et al. | |
| 6,304,764 B1 | 10/2001 | Pan | |
| 6,312,363 B1 * | 11/2001 | Watterson et al. | 482/54 |
| 6,344,727 B1 | 2/2002 | Desai et al. | |
| 6,353,894 B1 | 3/2002 | Pione | |
| 6,385,596 B1 | 5/2002 | Wiser et al. | |
| 6,453,371 B1 | 9/2002 | Hampson et al. | |
| 6,458,060 B1 * | 10/2002 | Watterson et al. | 482/54 |
| 6,464,618 B1 * | 10/2002 | Shea | 482/8 |
| 6,485,328 B1 | 11/2002 | Wu | |
| 6,489,751 B2 | 12/2002 | Small et al. | |
| 6,497,638 B1 * | 12/2002 | Shea | 482/8 |
| 6,526,287 B1 | 2/2003 | Lee | |
| 6,577,877 B1 | 6/2003 | Charlier et al. | |
| 6,591,085 B1 | 7/2003 | Grady | |
| 6,601,016 B1 * | 7/2003 | Brown et al. | 702/182 |
| 6,608,399 B2 | 8/2003 | McConnell et al. | |
| 6,629,197 B1 | 9/2003 | Bhogal et al. | |
| 6,634,992 B1 * | 10/2003 | Ogawa | 482/8 |
| 6,638,198 B1 * | 10/2003 | Shea | 482/8 |
| 6,653,813 B2 | 11/2003 | Khatri | |
| 6,665,803 B2 | 12/2003 | Lunsford et al. | |
| 6,674,995 B1 | 1/2004 | Meyers et al. | |
| 6,697,944 B1 | 2/2004 | Jones et al. | |
| 6,724,339 B2 | 4/2004 | Conway et al. | |
| 6,725,061 B1 | 4/2004 | Hutchison, IV et al. | |
| 6,728,546 B1 | 4/2004 | Peterson et al. | |
| 6,728,729 B1 | 4/2004 | Jawa et al. | |
| 6,747,859 B2 | 6/2004 | Walbeck et al. | |
| 6,761,635 B2 | 7/2004 | Hoshino et al. | |
| 6,799,226 B1 | 9/2004 | Robbin et al. | |
| 6,813,528 B1 | 11/2004 | Yang | |
| 6,816,376 B2 | 11/2004 | Bright et al. | |
| 6,830,160 B2 | 12/2004 | Risolia | |
| 6,859,538 B1 | 2/2005 | Voltz | |
| 6,931,456 B2 | 8/2005 | Payne et al. | |
| 6,939,177 B2 | 9/2005 | Kato et al. | |
| 6,991,483 B1 | 1/2006 | Milan et al. | |
| 6,997,852 B2 * | 2/2006 | Watterson et al. | 482/1 |
| 7,004,787 B2 | 2/2006 | Milan | |
| 7,050,783 B2 | 5/2006 | Curtiss et al. | |
| 7,054,888 B2 | 5/2006 | LaChapelle et al. | |
| 7,062,261 B2 | 6/2006 | Goldstein et al. | |
| 7,127,678 B2 | 10/2006 | Bhesania et al. | |
| 7,167,112 B2 | 1/2007 | Andersen et al. | |
| 7,167,935 B2 | 1/2007 | Hellberg | |
| 7,187,947 B1 | 3/2007 | White et al. | |
| 7,187,948 B2 | 3/2007 | Alden | |
| 7,215,042 B2 | 5/2007 | Yan | |
| 7,281,214 B2 | 10/2007 | Fadell | |
| 7,293,122 B1 | 11/2007 | Schubert et al. | |
| 7,293,227 B2 | 11/2007 | Plastina et al. | |
| 7,299,304 B2 | 11/2007 | Saint-Hilaire et al. | |
| 7,519,327 B2 * | 4/2009 | White | 455/41.2 |
| 7,537,546 B2 * | 5/2009 | Watterson et al. | 482/8 |
| 7,549,947 B2 * | 6/2009 | Hickman et al. | 482/8 |
| 7,556,590 B2 * | 7/2009 | Watterson et al. | 482/8 |
| 7,603,255 B2 * | 10/2009 | Case et al. | 702/182 |
| 7,618,345 B2 | 11/2009 | Corbalis et al. | |
| 7,628,730 B1 * | 12/2009 | Watterson et al. | 482/8 |
| 7,637,847 B1 * | 12/2009 | Hickman | 482/8 |
| 7,670,263 B2 | 3/2010 | Ellis et al. | |
| 2001/0003297 A1 | 6/2001 | Gilbert | |
| 2001/0005641 A1 | 6/2001 | Matsumoto et al. | |
| 2001/0006884 A1 | 7/2001 | Matsumoto | |
| 2002/0002035 A1 | 1/2002 | Sim et al. | |
| 2002/0029303 A1 | 3/2002 | Nguyen | |
| 2002/0065074 A1 | 5/2002 | Cohn et al. | |
| 2002/0068610 A1 | 6/2002 | Anvekar et al. | |
| 2002/0105861 A1 | 8/2002 | Leapman | |
| 2002/0115480 A1 | 8/2002 | Huang | |
| 2002/0132651 A1 | 9/2002 | Jinnouchi | |
| 2002/0151327 A1 | 10/2002 | Levitt | |
| 2002/0152874 A1 | 10/2002 | Vilcauskas et al. | |
| 2002/0156546 A1 | 10/2002 | Ramaswamy | |
| 2002/0156949 A1 | 10/2002 | Kubo et al. | |
| 2002/0173273 A1 | 11/2002 | Spurgat et al. | |
| 2002/0174269 A1 | 11/2002 | Spurgat et al. | |
| 2002/0194621 A1 | 12/2002 | Tran et al. | |
| 2003/0004934 A1 | 1/2003 | Qian | |
| 2003/0011608 A1 | 1/2003 | Wada | |
| 2003/0028664 A1 | 2/2003 | Tan et al. | |
| 2003/0041206 A1 | 2/2003 | Dickie | |
| 2003/0059022 A1 | 3/2003 | Nebiker et al. | |
| 2003/0067741 A1 | 4/2003 | Alfonso et al. | |
| 2003/0073432 A1 | 4/2003 | Meade | |
| 2003/0079038 A1 | 4/2003 | Robbin et al. | |
| 2003/0090988 A1 | 5/2003 | Chen | |
| 2003/0097379 A1 | 5/2003 | Ireton | |
| 2003/0110403 A1 | 6/2003 | Crutchfield et al. | |
| 2003/0151621 A1 | 8/2003 | McEvilly et al. | |
| 2003/0172209 A1 | 9/2003 | Liu et al. | |
| 2003/0185395 A1 | 10/2003 | Lee et al. | |
| 2003/0198015 A1 | 10/2003 | Vogt | |
| 2003/0220988 A1 | 11/2003 | Hymel | |
| 2003/0236075 A1 | 12/2003 | Johnson et al. | |
| 2003/0237043 A1 | 12/2003 | Novak et al. | |
| 2004/0003300 A1 | 1/2004 | Malueg et al. | |
| 2004/0019497 A1 | 1/2004 | Volk et al. | |
| 2004/0039860 A1 | 2/2004 | Mills et al. | |
| 2004/0048569 A1 | 3/2004 | Kawamura | |
| 2004/0090998 A1 | 5/2004 | Chen | |
| 2004/0102931 A1 | 5/2004 | Ellis et al. | |
| 2004/0103223 A1 | 5/2004 | Gabehart et al. | |
| 2004/0116005 A1 | 6/2004 | Choi | |
| 2004/0162029 A1 | 8/2004 | Grady | |
| 2004/0186935 A1 | 9/2004 | Bel et al. | |
| 2004/0194154 A1 | 9/2004 | Meadors et al. | |
| 2004/0224638 A1 | 11/2004 | Fadell et al. | |
| 2004/0249994 A1 | 12/2004 | Shapiro et al. | |
| 2004/0252966 A1 | 12/2004 | Holloway et al. | |
| 2004/0267812 A1 | 12/2004 | Harris et al. | |
| 2004/0267825 A1 | 12/2004 | Novak et al. | |
| 2005/0014531 A1 | 1/2005 | Findikli | |
| 2005/0015355 A1 | 1/2005 | Heller et al. | |
| 2005/0022212 A1 | 1/2005 | Bowen | |
| 2005/0135790 A1 | 6/2005 | Hutten | |
| 2005/0149213 A1 | 7/2005 | Guzak et al. | |
| 2005/0181756 A1 | 8/2005 | Lin | |
| 2005/0207726 A1 | 9/2005 | Chen | |
| 2005/0209050 A1 * | 9/2005 | Bartels | 482/8 |
| 2005/0233861 A1 * | 10/2005 | Hickman et al. | 482/8 |
| 2005/0239333 A1 | 10/2005 | Watanabe et al. | |
| 2005/0239601 A1 * | 10/2005 | Thomas | 482/1 |
| 2005/0240705 A1 | 10/2005 | Novotney et al. | |
| 2005/0266961 A1 | 12/2005 | Shum et al. | |

| | | | |
|---|---|---|---|
| 2005/0281185 A1 | 12/2005 | Kawasaki | |
| 2005/0288154 A1* | 12/2005 | Lee et al. | 482/3 |
| 2006/0031545 A1 | 2/2006 | Manders et al. | |
| 2006/0063644 A1 | 3/2006 | Yang | |
| 2006/0063645 A1* | 3/2006 | Chiang | 482/8 |
| 2006/0088228 A1 | 4/2006 | Marriott et al. | |
| 2006/0156415 A1 | 7/2006 | Rubinstein et al. | |
| 2006/0161621 A1 | 7/2006 | Rosenberg | |
| 2006/0163358 A1 | 7/2006 | Biderman | |
| 2006/0205569 A1* | 9/2006 | Watterson et al. | 482/54 |
| 2006/0247851 A1 | 11/2006 | Morris | |
| 2006/0258289 A1 | 11/2006 | Dua | |
| 2006/0294209 A1 | 12/2006 | Rosenbloom et al. | |
| 2007/0049462 A1* | 3/2007 | Asukai et al. | 482/8 |
| 2007/0056013 A1 | 3/2007 | Duncan | |
| 2007/0080823 A1 | 4/2007 | Fu et al. | |
| 2007/0083814 A1 | 4/2007 | Wilbrink et al. | |
| 2007/0086724 A1 | 4/2007 | Grady et al. | |
| 2007/0135264 A1 | 6/2007 | Rosenberg | |
| 2007/0173197 A1 | 7/2007 | Hsiung | |
| 2007/0173294 A1 | 7/2007 | Hsiung | |
| 2007/0206827 A1 | 9/2007 | Tupman et al. | |
| 2007/0219059 A1* | 9/2007 | Schwartz et al. | 482/8 |
| 2007/0226384 A1 | 9/2007 | Robbin et al. | |
| 2007/0236482 A1 | 10/2007 | Proctor et al. | |
| 2007/0265138 A1* | 11/2007 | Ashby | 482/8 |
| 2007/0270663 A1 | 11/2007 | Ng et al. | |
| 2007/0270721 A1 | 11/2007 | Ananny et al. | |
| 2007/0271065 A1 | 11/2007 | Gupta et al. | |
| 2007/0271387 A1 | 11/2007 | Lydon et al. | |
| 2008/0090703 A1 | 4/2008 | Rosenberg | |
| 2009/0111656 A1* | 4/2009 | Sullivan et al. | 482/4 |
| 2009/0118100 A1* | 5/2009 | Oliver et al. | 482/8 |

FOREIGN PATENT DOCUMENTS

| | | |
|---|---|---|
| EP | 1367734 A1 | 12/2003 |
| EP | 1498899 A1 | 1/2005 |
| EP | 1594319 A1 | 11/2005 |
| EP | 1672613 A2 | 6/2006 |
| EP | 1755098 A2 | 2/2007 |
| EP | 1925341 A1 | 5/2008 |
| GB | 2405718 A | 3/2005 |
| JP | 11-288420 A | 10/1999 |
| JP | 2000-214953 A | 8/2000 |
| JP | 2001-069165 A | 3/2001 |
| JP | 2002-252566 A | 9/2002 |
| JP | 3090747 U | 10/2002 |
| JP | 2002-342659 A | 11/2002 |
| JP | 2002-374447 A | 12/2002 |
| JP | 2003-032351 A | 1/2003 |
| JP | 2003-274386 A | 9/2003 |
| WO | WO 99-26330 A2 | 5/1999 |
| WO | WO 00-39907 A1 | 7/2000 |
| WO | WO 00-60450 A1 | 10/2000 |
| WO | WO 02-49314 A2 | 6/2002 |
| WO | WO 03-036541 A1 | 5/2003 |
| WO | WO 03-036957 A1 | 5/2003 |
| WO | WO 03-073688 A1 | 9/2003 |
| WO | WO 2004-084413 A2 | 9/2004 |
| WO | WO 2004-112311 A1 | 12/2004 |
| WO | WO 2005-119463 A2 | 12/2005 |
| WO | WO 2006-080957 A2 | 8/2006 |
| WO | WO 2006-104478 A1 | 10/2006 |
| WO | WO 2008-030484 A2 | 3/2008 |
| WO | WO 2008-036275 A2 | 3/2008 |
| WO | WO 2008-101168 A2 | 8/2008 |

OTHER PUBLICATIONS

"A Serial Bus on Speed Diagram: Getting Connected with FireWire," downloaded Oct. 16, 2001, PC Magazine: PC Tech (A Serial Bus on Speed) wysiwyg:--51http:--www.zdnet.com-pctech-content-18-10-tu1810.007.html p. 7.

Belkin iPod Voice Recorder, Product Specification Sheet, printed Jun. 16, 2004.

Bindra, "Standard Turns Monitor into I-O Hub," Electronic Engineering Times, vol. 918, Sep. 6, 1996, p. 14.

Brentrup, "Introduction to Public Key Cryptography Demystified," Campus Technology, printed from http:--www.campus-technology.com-article.asp?id=7626 on Oct. 6, 2004.

Brown, "Making UBS Work," downloaded Oct. 16, 2001, PC Magazine: PC Tech wysiwyg:-155-http:--www.zdnet.com-pcmag-pctech-content!18-04-tu1804.001.html.

"Cables to Go," download Oct. 16, 2001 http:--www.cablestogo.com-product.asp?cat%5Fid=601&sku=27028.

Crawford et al., "Sample rate conversion and bit rate reduction in the studio," IEE Colloquim on Digital Audio Signal Processing, May 22, 1991, pp. 8-1-8-3.

Derman, "Monitors Make Net Connections," Electronic Engineering Times, vol. 933, 1996, pp. 60 and 69.

"ExpressBus™ F5U0I0," User Guide Packing Checklist, Belkin Components Product Warranty.

"FireWire", downloaded Oct. 16, 2001, si wyg:- -4 2-http:--developer.apple. comlhardwarelFire Wire.

"Fire Wire Connector," downloaded Oct. 16, 2001, wysiwyg:--76-http:--developer.apple.com-...es-Macintosh_CPUs-G3-ibook-ibook-27.html.

Fried, "FireWire poised to become ubiquitous," downloaded Oct. 16, 2001, CNET News.com, 1394 Trade Association: Press, wysiwyg:-132-http:- 113 94ta.org-Press-200 1 Press-august!8.2 7.b.html.

Fried, "New Fire Wire to blaze faster trail," downloaded Oct. 16, 2001, CNET News.com, http:--news.cnet.com-news-0-I006-200-6021210.html.

"How to Connect Your Computer PC Hardware", downloaded Oct. 16, 2001, http:---www.scar.utoronto.ca!~ccweb-faculty-connect-howto.html.

"IEEE 1394-USB Comparison," downloaded Oct. 16, 2001, www.genitech.com.aulLIBRARY-TechSupportiinfobits-firewirevsusb.html.

"Introduction to Public Key Cryptography," Oct. 9, 1998, printed from http:--developer.netscape.com-docs-manuals-security-pkin-contents.html on Oct. 6, 2004.

iPod Classic User's Guide, acquired from apple.com, 2002; 44 pages.

iPod nano Features Guide, acquired from apple.com, 2008; 72 pages.

iPod touch User's Guide, acquired from apple.com, 2008, 120 pages.

"iPodDock-iPod Cradle," www.bookendzdocks.com-bookendz-dock_cradle.html, downloaded Feb. 27, 2003.

Lambert, "Digital Audio Interfaces," Journal of the Audio Engineering Society, Audio Engineering Society, New York, NY, vol. 38, No. 9, (Sep. 1, 1990), pp. 681-684, 686, 688, 690, 692 and 696, ISSN: 1549-4950 figures 9, 10.

Lewis, "On Technology" Fortune Magazine, Dec. 9, 2002, p. 240.

Menezes et al., "Handbook of Applied Cryptography," Identification and Entity Authentication, pp. 385-424.

Microsoft, "Media Transport Protocol Implementation Details," 2005, 18 pages.

"MPV™ Music Profile Specification Revision 1.00" Internet Citation [online] (Jan. 7, 2004) URL:http--www.osta.org-mpv-public-specs-MPVMusic-Prof-Spec-1.00.pdf> [retrieved Jun. 20, 2006] the whole document, 70 pages.

Networking Tech Note, "1394 Standards and Specifications," 3 pages.

"Neuros MP3 Digital Audio Computer," www.neurosaudio.com, downloaded Apr. 9, 2003, 6 pages.

"PMC FW2 IEEE1394 FireWire Controller", downloaded Oct. 16, 2001, http:--www.bvmltd.co.uk-PMCfw2ds.html.

Severance, "FireWire Finally Comes Home," Michigan State University, Standards, Nov. 1998, pp. 117-118.

Sinitsyn, "Synchronization Framework for Personal Mobile Servers," Pervasive Computing and Communications Workshops (PERCOMW'04), Proceedings of the Second IEEE Annual Conference, Piscataway, NJ, USA, IEEE, Mar. 14, 2004, pp. 208-212.

Teener, "Understanding Fire Wire: The IEEE 1394 Standards and Specifications," downloaded Oct. 16, 2001, wysiwyg:119-http:1 lwww.chipcenter.com-networking-ieee 1394-main.html.

"The Authoritative Dictionary of IEEE Standards Terms, Seventh Edition," Published by Standards Information Network, IEEE Press, 2000, 3 pages.

"Universal Serial Bus Specification—Rev 2.0," Chapter 6, Compaq Hewlett-Packard, Apr. 27, 2000, pp. 85, 99-100.

"Universal Serial Bus Specification—Rev 2.0," Chapter 9, USB Device Framework, no date, pp. 239-274.

Vitaliano, "Why FireWire is Hot!Hot!Hot!" downloaded Oct. 16, 2001, "Impact.FireWire.SideBar" http:--www.vxm.com-21R.35.html.

Whittle, "Public Key Authentication Framework: Tutorial," First Principles Consulting, Jun. 2, 1996, downloaded Oct. 6, 2004, http:--www.ozemail.com.au-~firstpr-crypto-pkaftute.htm, 7 pages.

International Application No. PCT/US2009/032052, International Search Report and Written Opinion, 16 pages, Jul. 9, 2009.

U.K. Application No. GB0902820.0, Combined Search and Examination Report, 7 pages, Jun. 16, 2009.

"Nokia 5140 Mobile Phone Adds Mobility to Outdoor Adventure, Sport and Fitness", dated Feb. 2, 2004, 2 pages Retrieved from http://press.nokia/PR/200402/932564_5.html on May 26, 2010.

* cited by examiner

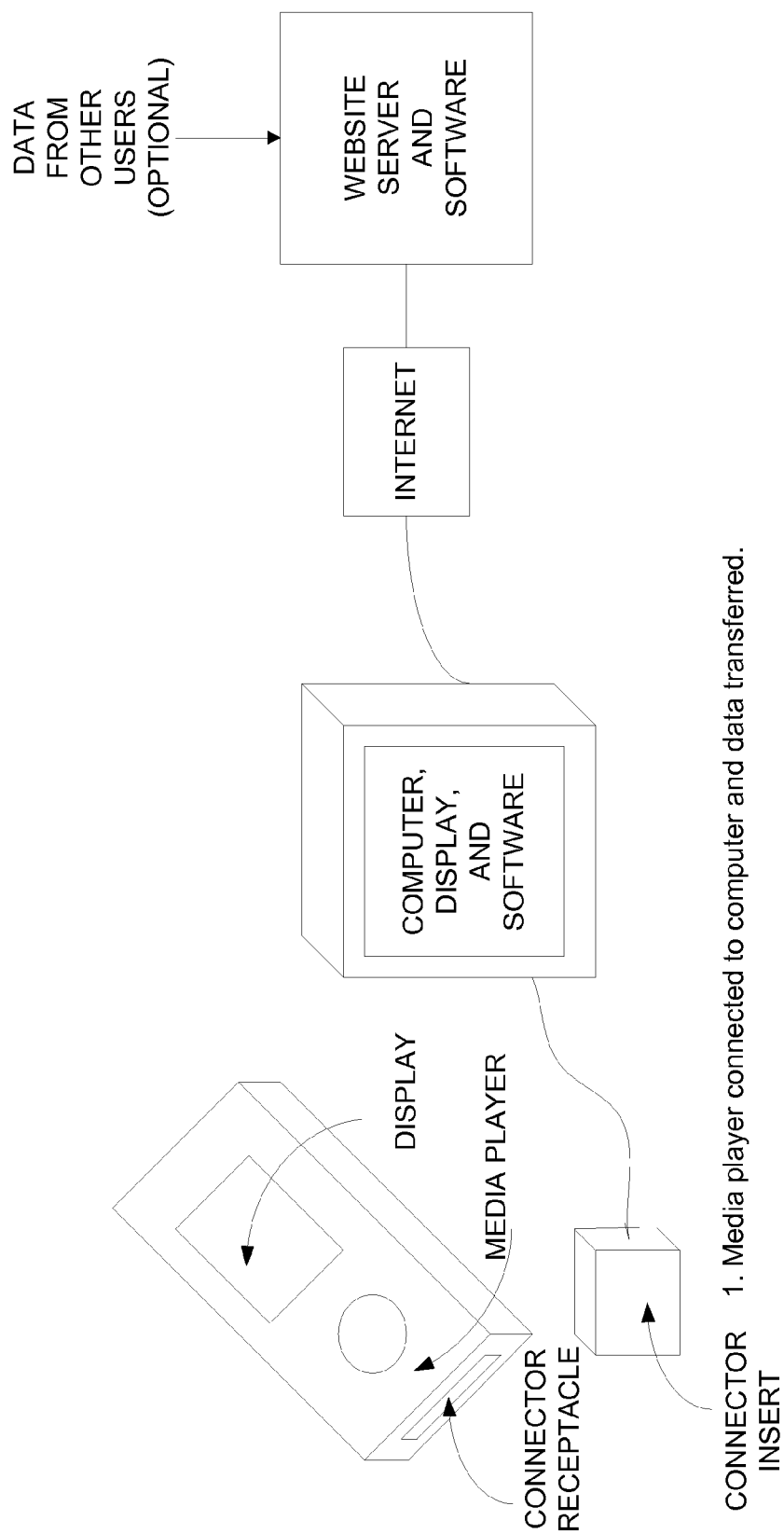

| GYM DATA 1200 |
| --- |
| EQUIPMENT INFORMATION 1220 |

| EQUIPMENT INFORMATION |
| --- |
| MANUFACTURER ID |
| MANUFACTURER NAME |
| EQUIPMENT TYPE |
| EQUIPMENT NAME/MODEL |
| SERIAL NUMBER |
| GYM NAME |
| GYM LOCATION |
| EQUIPMENT INFORMATION |

| USER INFORMATION 1230 |
| --- |

| USER INFO |
| --- |
| NAME |
| WEIGHT |
| GENDER |
| USER INFO |

| WORKOUT TEMPLATE 1240 |
| --- |

| TEMPLATE |
| --- |
| NAME |
| CALORIC GOAL |
| TIME GOAL |
| DISTANCE GOAL |
| SPEED GOAL |
| HEART RATE GOAL |
| TEMPLATE |

| INTERVAL DATA 1250 |
| --- |

| INTERVAL |
| --- |
| CURRENT CALORIES |
| CURRENT ELAPSED TIME |
| CURRENT DISTANCE |
| CURRENT SPEED |
| CURRENT HEART RATE |
| INCLINE |
| RESISTANCE / EFFORT |
| INTERVAL |

| WORKOUT SUMMARY 1270 |
| --- |

| WORKOUT |
| --- |
| TOTAL CALORIES |
| TOTAL ELAPSED TIME |
| TOTAL DISTANCE |
| AVERAGE SPEED |
| WORKOUT |

| MEDIA PLAYER INFO 1280 (WRITTEN BY MEDIA PLAYER) |
| --- |

| MEDIA PLAYER INFO |
| --- |
| START TIME/DATE |
| END TIME/DATE |
| MODEL |
| SOFTWARE VERSION |
| SERIAL NUMBER |
| MEDIA PLAYER INFO |

| SIGNATURE 1290 (WRITTEN BY MEDIA PLAYER) |
| --- |

| SIGNATURE |
| --- |

| GYM DATA 1295 |
| --- |

FIGURE 12

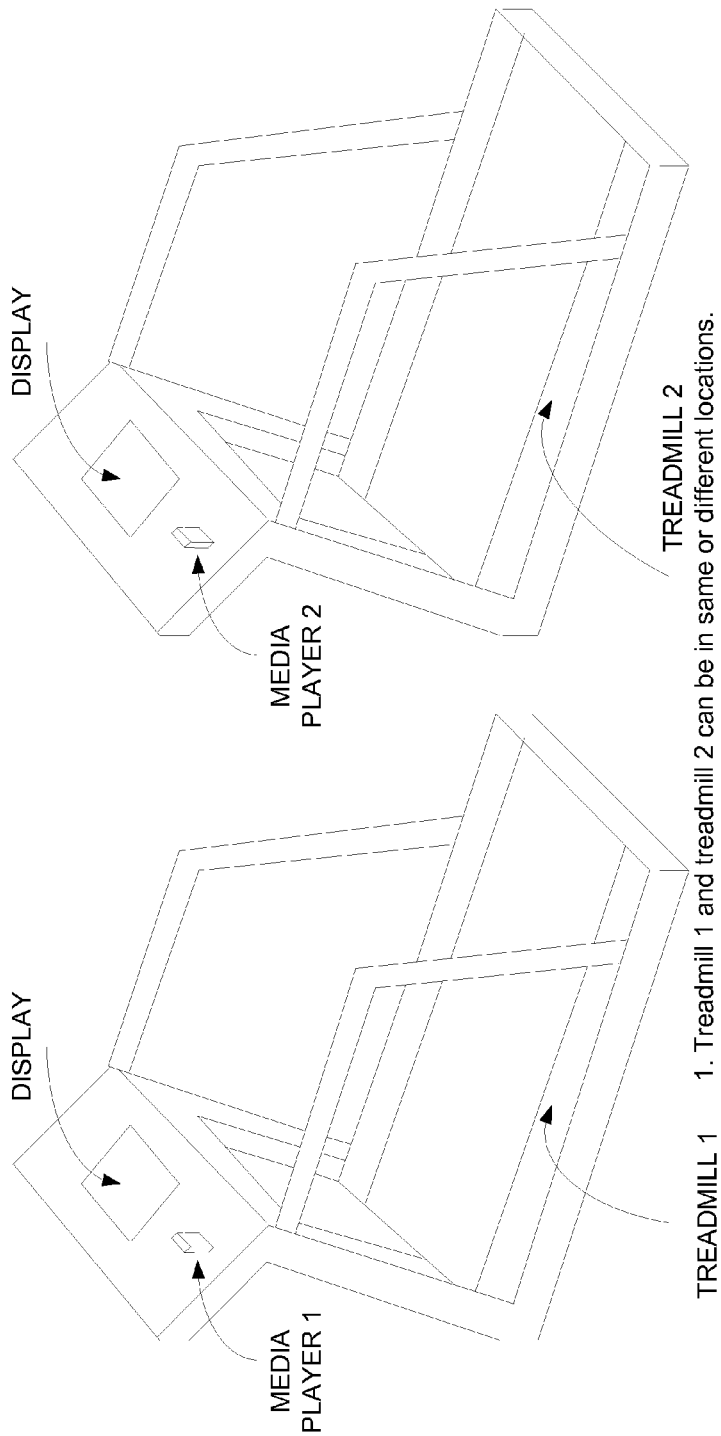

US 8,047,966 B2

INTERFACING PORTABLE MEDIA DEVICES AND SPORTS EQUIPMENT

CROSS-REFERENCES TO RELATED APPLICATIONS

This application claims the benefit of U.S. provisional application No. 61/032,805, filed Feb. 29, 2008, titled "Interfacing Portable Media Devices and Sports Equipment," which is incorporated by reference.

BACKGROUND

Portable media players have become very popular the past few years and their market penetration shows no signs of abating. People use them when walking, driving, and commuting by bus or train. They are also particularly useful as a distraction or source of entertainment when working out. People often bring these to a gym or similar location to use while exercising.

While exercising, many people like to keep track of their progress. For example, the distance "traveled" while on a treadmill may be recorded and progress over time monitored. This can provide positive feedback when progress is made; it can also provide encouragement to improve when efforts have been somewhat lacking.

This data is typically recorded using a clipboard and paper or notebook. However, this is somewhat time consuming. Because people often carve a few minutes out of their day to exercise, it is not desirable to lose time keeping track of this data; they may need to quickly return to work or home. Also, since it does not happen automatically, such record keeping can become spotty at times.

The portable media players that are often found at the gym are capable of carrying data. Unfortunately, there is currently no simple way to transfer workout data to them. That is, there is no easy way to transfer data from equipment in the gym to a portable media player.

Further, it would be desirable to store other types of data using a media player. For example, heart rate, blood pressure, blood oxygen level, and other monitors and sensors provide data that could be collected and stored.

Thus, what is needed are circuits, methods, and apparatus that allow sports and other types of equipment, such as the above-mentioned treadmill, to write data to a media player for record-keeping and other purposes.

SUMMARY

Accordingly, embodiments of the present invention provide circuits, methods, and apparatus that allow sports and other types of equipment, such as gym or other cardio equipment, to write data to a media player. Embodiments of the present invention further provide for the uploading of this data to a computer and third-party website. To monitor progress and provide encouragement, the third-party website can be used to track workout data over time. The third party-website can also collect data from other users. This is particularly useful in providing a competitive environment to encourage progress. This data can then be graphically displayed in various ways using the computer.

An exemplary embodiment of the present invention provides sports equipment that is capable of writing workout data to a media player. The workout data may be data related to contemporaneous workout activity. The sports equipment may include a connector or connector insert for mating to a connector receptacle on a media player to form a communication link. The sports equipment may also have wireless or optical circuitry that may be used to establish a communication link with the media player.

Once a communication link is established, user information may be retrieved from either the media player or sports equipment. A workout regime may also be selected. In various embodiments of the present invention, media on the media player can be read by the sports equipment and provided to the user.

A user may end a workout session at any time and disconnect the media player from the sports equipment. Accordingly, data is typically written from the sports equipment to the media player on a periodic basis. This prevents the loss of most of the workout data that would otherwise occur if the sports equipment waited until the end of a workout to write data.

Another exemplary embodiment of the present invention provides the uploading of this data to a user's computer. The computer may also track past workout data. This data may be graphically presented to the user. Reminders and encouragement may also be provided to the user, for example, using a display, speakers, headphone jack, or other interface.

Another exemplary embodiment of the present invention also provides the uploading of this data to a user's computer. The data can be further uploaded to a third-party website. The website may track past workout data. The website may also track other user's data. Current and past data may be provided to the user to show progress and provide encouragement. User workout data may be compared to data from other users to show competition progress and results. This information may be provided for viewing on the user's computer.

Another exemplary embodiment of the present invention provides real-time, head-to-head competition. These competitions may be between two or more people in one or more locations. Competition data may be shared and displayed to each user. Data may be shared using a wired, wireless, or optical link over a cellular, Internet, LAN, or other type of network.

Various embodiments of the present invention may incorporate one or more of these and the other features described herein. A better understanding of the nature and advantages of the present invention may be gained by reference to the following detailed description and the accompanying drawings.

BRIEF DESCRIPTION OF THE DRAWINGS

FIG. 6 illustrates the use of a third-party website in displaying workout data according to an embodiment of the present invention;

FIG. 7A illustrates a method of using a third-party website to display workout data according to an embodiment of the present invention, while

FIG. 12 illustrates data that may be written to a media device memory by sports equipment before, during, and after a workout session according to an embodiment of the present invention;

FIG. 13 illustrates a system including two items of sports equipment that may be used for real-time competitions;

DESCRIPTION OF EXEMPLARY EMBODIMENTS

Figure 1:
FIG. 1 illustrates a method of using a media player to record workout data according to an embodiment of the present invention.

FIG. 1 illustrates a method of using a media player to record workout data according to an embodiment of the present invention. This figure, as with the other included figures, is shown for illustrative purposes and does not limit either the possible embodiments of the present invention or the claims.

In this method, a media player records data provided by sports or other gym equipment. This data is then transferred to a computer. The data is then uploaded to a website, where it is combined with previous data as available, and downloaded to the computer and presented in a graphical fashion.

Specifically, in act 110, a communication link is established between a media player and an item of sports equipment. This communication may be wired or wireless. For example, it may be established by using a connector such as the 30 pin connector described in copending U.S. patent application Ser. No. 10/423,290, filed Apr. 25, 2003, titled Media Player, which is incorporated by reference. The communication link may alternatively be wireless or optical in nature. The link may be used to download workout data from the sports equipment to the media player. Also, other types of information may be exchanged between the media player and the sports equipment. For example, the sports equipment may be located in a gym or hotel. In such a situation, it may be desirable that local news, weather, and information regarding the gym or hotel be placed on the media player.

The link may also include power supply circuitry to charge the media player. The power supply charging circuitry may provide DC power, or it may provide inductive charging. The sports equipment may derive the charging power from a power source. Alternatively, user interaction with the equipment may be used to create the power source, particularly where a physical connection is not practical, for example, on a bicycle. In this case, a generator that derives power from a spinning wheel or other moving part can be attached to the sports equipment, be it a treadmill, bicycle, or other type of equipment. The power thus generated can then be used to charge the media player.

The media player may be a media player such as an iPod or iPhone manufactured by Apple Inc. of Cupertino, Calif. Alternatively, other types of phones, media players, personal digital assistants, or other electronic devices may be used.

The sports equipment may be gym equipment, such as a treadmill, elliptical stepper, stationary bicycle, weight machine, or other gym or cardio equipment. The sports equipment may be other types of sports equipment, such as bicycles or other sports or cardio equipment. Also, while embodiments of the present invention are particularly suited to recording data provided by sports equipment, data from other sources may be recorded as well. For example, data from monitors, detectors, sensors, or other measuring or other types of equipment may also be recorded and placed on the media player.

The sports equipment may be located in a traditional location such as a gym. The equipment may also be located in workplace or hotel workout areas. The sports equipment may be for personal use and located in a home, or used by individuals in public places. For example, the equipment may be a bicycle.

The data may be data generated by the sports equipment by measuring physical movement of a portion of the sports equipment being acted on by a user. This physical movement may be angular, linear, or have other directional qualities. For example, a user may spin a wheel on a bicycle. Alternatively, the user may cause one or more wheels to spin on a treadmill. These physical activities can then be translated by circuitry in or associated with the sports equipment into data to be written to the media player. The data may be written by the same or other circuits on or associated with the sports equipment. The translation from physical movement to workout data may include or account for user profile data such as weight, height, or other attributes or types of data.

It is often desirable that this recorded data be associated with a particular user. Accordingly, in act 120, user data, such as user profile data, is either entered or recalled from memory. The user data may include user profile data such as a user name, nickname, or other identification, age, weight, gender, or other user data. The user data may be entered using the sports equipment, media player, computer, or other device. This information may alternatively be entered before the communications link is established in act 1 10. For example, it may be desirable for a user to enter certain information at home while the media player is connected to a computer before the user goes to a gym for a workout.

This data may be newly entered, or it may be retrieved from memory located either on the media player or the sports equipment. In some instances where a user may be limited in time, it may be desirable to collect and store this user data while the workout is proceeding. Alternatively, for safety reasons, it may be desirable to collect this data either after or before the workout. In some embodiments of the present invention, user data for more than one user may be stored on a media player. Accordingly, act 120 may consist of asking the user to identify herself from a list of possible users.

Once communication is established between a media player and sports equipment, data may be recorded by the sports equipment on the media player. Accordingly, in act 130, workout data is recorded by the sports equipment on the media player. Typically, this data is recorded on a periodic basis. This prevents large amount of workout data from being lost if communication between the media player and sports equipment is broken. Specifically, only the amount of data generated since the last write cycle is lost when the user removes or otherwise breaks the communication link between the media player and the sports equipment. For example, a user may abruptly remove the media player at a time before what the sports equipment may expect. The user may be dissatisfied if the workout data is not recorded on the media player due to its removal. Accordingly, a specific embodiment of the present invention records data every 10 seconds, though other embodiments may record the data every 20 seconds, or on another periodic basis.

In act 140, the workout data is transferred to a user's computer. The data may be transferred using software, such as iTunes, a product of Apple Inc. of Cupertino Calif. The software program used to transfer the workout data may be the same software program that is used to write data and media to the media player. In other embodiments of the present invention, the workout data is transferred to the user's computer in real-time, for example, using a wireless link between the media player or sports equipment and the user's computer.

Once the data is transferred to a user's computer, it is desirable to make this data available to the user in a graphical format. For example, a graphical format may be useful in encouraging the user to continue with a workout regiment. In this specific example, the data is uploaded to a server where it is formatted graphically and downloaded to the user's computer for viewing. Alternatively, this may be done on the user's computer. Moreover, some or all of this may be done on the media player itself.

Specifically, in act 150, workout data is uploaded from the user's computer to a website server. This data may be combined with previous data retrieved from the server memory in act 160. This is particularly useful in showing a user's workout progress. Also, data from other users may be provided as well. This is particularly useful in providing a competitive setting. For example, it may be desirable to track which of the number of users is the first to reach a certain number of miles on a treadmill.

Again, for encouragement purposes, it is often desirable to show such workout data, including progress and competition data, in a graphical format. Accordingly, in act 170, the graphical data is downloaded from the server to the user's computer.

Again, the equipment may be sports equipment or other types of equipment. The sports equipment may be gym equipment, or other type of equipment, such as a bicycle. One type of gym equipment that is particularly suited to an embodiment of the present invention is the treadmill. An example is shown in the following figure.

Figure 2:
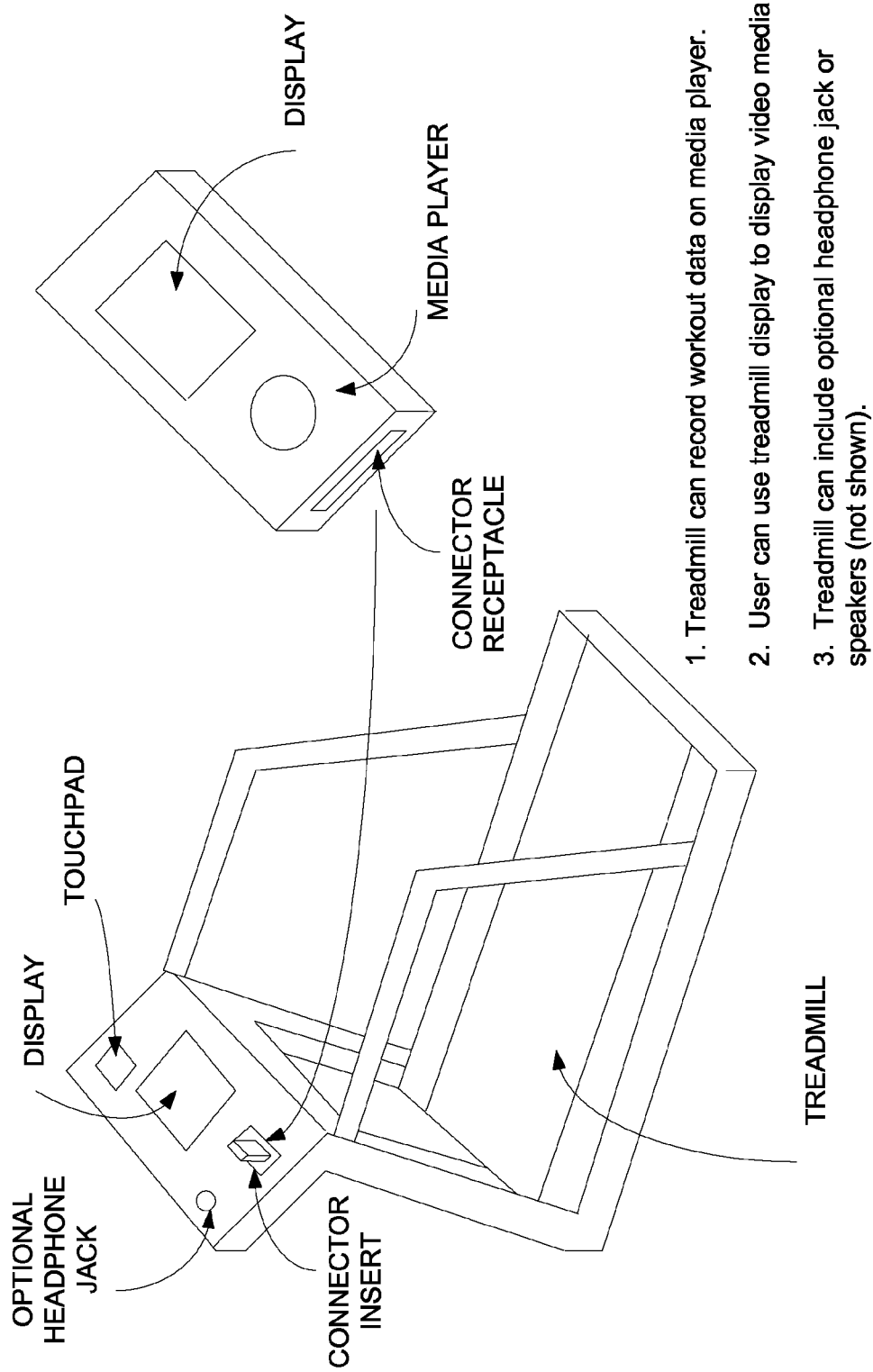
FIG. 2 illustrates a data workout recording system including a media player and sports equipment according to an embodiment of the present invention.

FIG. 2 illustrates a data workout recording system including a media player and sports equipment according to an embodiment of the present invention. This figure includes a media player and a treadmill. The media player includes a display, touchpad, and a connector receptacle. The treadmill includes a connector insert, typically located in a recessed portion of the treadmill, and an optional display. In various embodiments of the present invention, some sports equipment may not have a display. Alternatively, other sports equipment may have a simple display, for example, one formed using a number of LEDs. Still other embodiments may include an LCD or other type of display, while still other higher-end units may include a touchscreen display.

User data, prompts, and other information may be generated and displayed using either the media player or the display on the treadmill. The treadmill may also have other means of receiving input data, in this example, the touchpad. The touchpad may be a keypad or other such tactile interface, or it may be another type of data entry interface.

The user can establish communication between the media player and the treadmill by inserting the connector insert of the treadmill into the connector receptacle of the media player. Again, the treadmill insert may be recessed for mechanical stability reasons. While the workout is underway, the treadmill can record workout data on the media player.

A user may also wish to enjoy the media stored on the media player while the workout is progressing. Accordingly, embodiments of the present invention may also include items such as a headphone jack or speakers (not shown.) Also, the display, if available, may be used to view video or other media. The touchpad or touchscreen, if available, can be used to enter user data, select workout routines, or select and control media from the media player. These various activities are shown further in the following figure.

Figure 3:
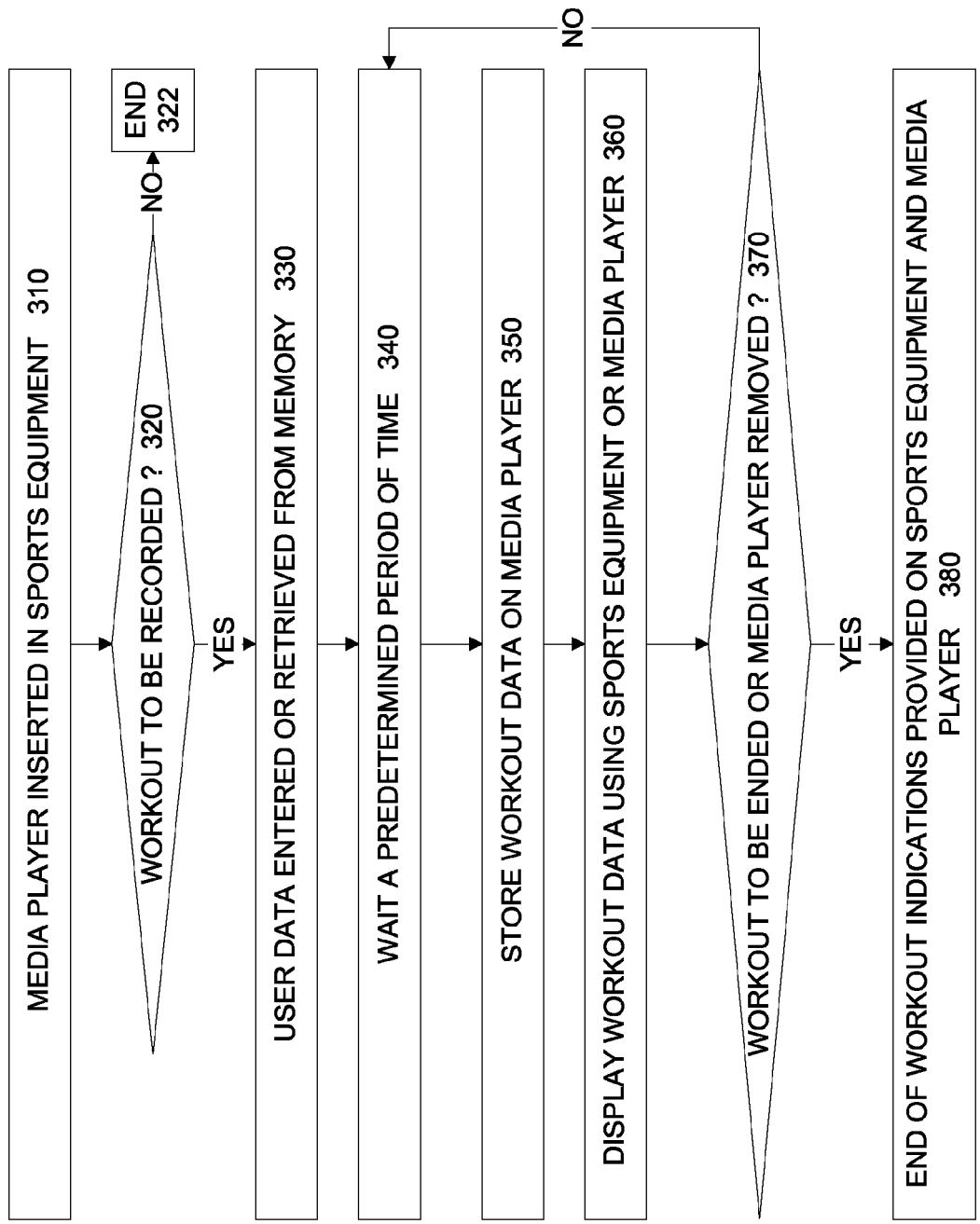
FIG. 3 illustrates a method of using a media player to store workout data according to an embodiment of the present invention.

FIG. 3 illustrates a method of using a media player to store workout data according to an embodiment of the present invention. In this figure, the media player is inserted in the sports equipment. During the workout, data is written to the media player.

Specifically, in act 310, the media player is inserted into the sports equipment, for example, the treadmill in FIG. 2. Again, in other embodiments of the present invention, communication may be established in other ways. For example, wireless, optical, or other wired connections may be used. Alternatively, the media player may be attached to a cable or other electronic device that is in communication with the sports equipment.

In act 320, the user is prompted as to whether the workout should be recorded. For example, the user may simply insert the media player in order to watch a movie or listen to music during her workout. If the workout is not to be recorded, no further activity is performed, as shown in act 322. If the workout is to be recorded, user data is entered or retrieved from memory in act 330. Again, this may include entering data using the media player or sports equipment, or selecting a user from a list of possible users.

Once a workout commences, data is typically written to the media player on a periodic basis. Again, a user, at the completion of a workout, may simply remove the media player without warning or being prompted by the sports equipment. It is therefore undesirable to wait until the end of the workout session to write data to the media player. Accordingly, in act 340, it is determined that a predetermined amount of time, in one specific example, 10 seconds, has passed, thus the workout data is stored on the media player by the sports equipment in act 350. In other embodiments of the present invention, other periods of time, such as 20 seconds, may be used, that is, data may be written by the sports equipment to the media player every 20 seconds.

It may also be desirable to display workout data to the user while the workout is progressing. For example, speed, calories burned, and the like it may be displayed. Further, other information, for example, information from other users, may also be provided for competitive purposes. Previous information generated by the user may be displayed to show progress.

In act 370, it is determined whether the workout has ended or the media player has been removed. If not, data is written after the predetermined time has elapsed. When the workout ends, workout indications may be provided on the treadmill or media player. Such indications may be messages such as "congratulations," "good work," and the like, and these may be used to provide encouragement to the user.

Workout data collected in this way may be viewed using the media player. However, it is desirable to transfer this data from the media player to a computer, which typically has more storage space, in order to free memory space on the media player for the next workout, or for storing media or other content. Also, for encouragement purposes, it is desirable to view the data in a more sophisticated graphical context. Accordingly, workout data is typically moved to a user's computer. An example is shown in the following figure.

Figure 4:
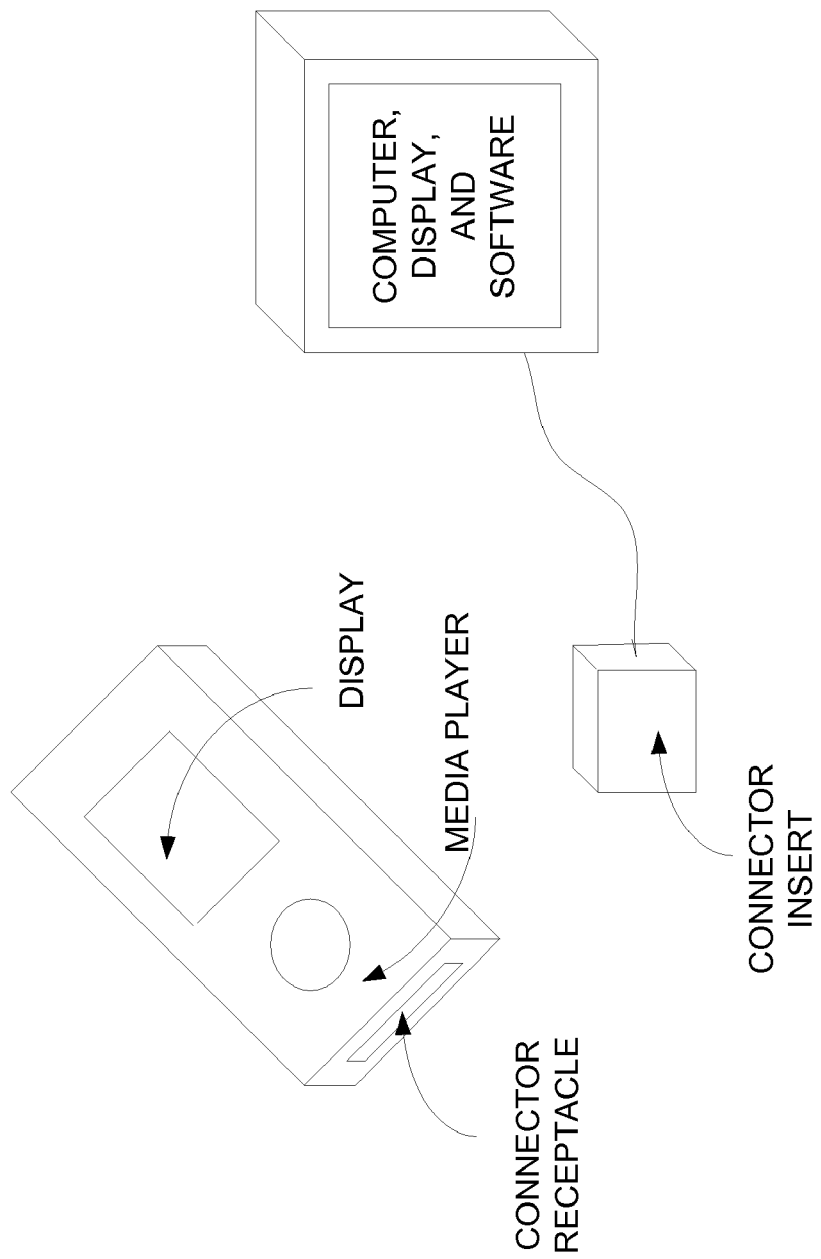
FIG. 4 illustrates a system for uploading workout data from a media player to a computer.

FIG. 4 illustrates a system for uploading workout data from a media player to a computer. In this example, the workout or other data collected above can be transferred from the media player to a user's computer. Also, data from the computer may be loaded onto the media player. For example, information may be entered by the user on the computer. This information may in turn be loaded onto the media player. Again, the media player typically includes a connector receptacle. A cable having a connector insert on a first end and a second connector, such as a USB or FireWire connector appropriate for connecting to a computer on a second end. This cable may be used to form a wired connection between the computer and the media player. Alternatively, wireless or optical communications may be used to transfer data between the media player and the user's computer. A software program resident on the computer can then process the data. The computer can then display the data in a graphical format. This data may include recent workout data, as well as workout data from prior workout sessions to show user progress. These acts are shown further in the following figure.

Figure 5:
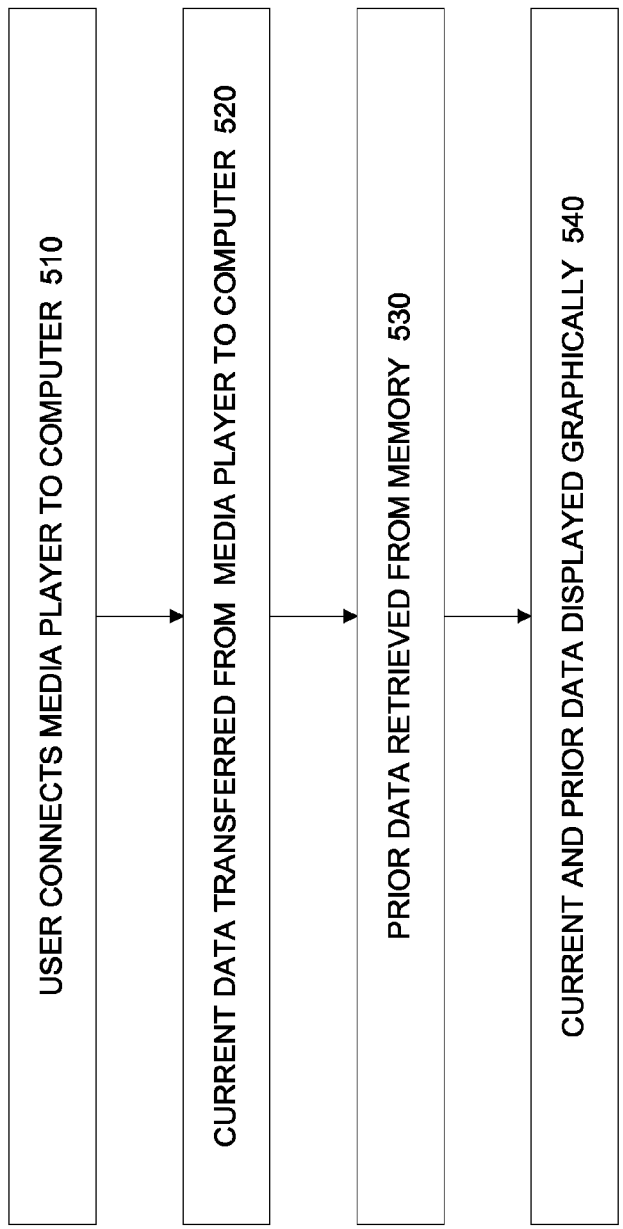
FIG. 5 is a flowchart illustrating a method of transferring data to a user's computer according to an embodiment of the present invention.

FIG. 5 is a flowchart illustrating a method of transferring data to a user's computer according to an embodiment of the present invention. In act 510, the user connects the media player to a computer. This connection may be a physical connection, or wireless, optical or other type of connection. Current data is transferred from the media player to the computer in act 520. Prior data may be retrieved from memory in act 530. Current and prior data may be displayed graphically in act 540.

It may be further desirable to upload workout data to a third-party website. This is particularly useful as it allows third-party information to be provided to the user. Also, workout data from other users may be provided by the website for competition purposes. An example of this is shown the following figure.

FIG. 6 illustrates the use of a third-party website in displaying workout data according to an embodiment of the present invention. As before, a connection is made between a user's computer and media player. Data can be transferred from the media player to the user's computer. This data can be further uploaded via the Internet to a third-party website. The third-party website can retrieve previous workout data and present this data to the user. Again, this is particularly useful to show use progress. Data from other users may be included as well. This is useful to show competitive results. These activities are shown in the following figure.

Figure 7B:
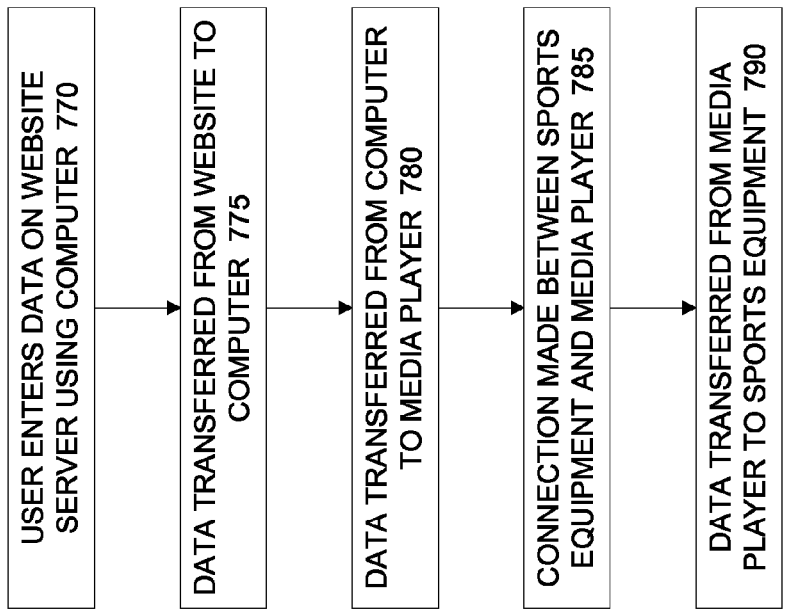
FIG. 7B illustrates a method of transferring data from a user's computer to sports equipment via a website according to an embodiment of the present invention.
Figure 7A:
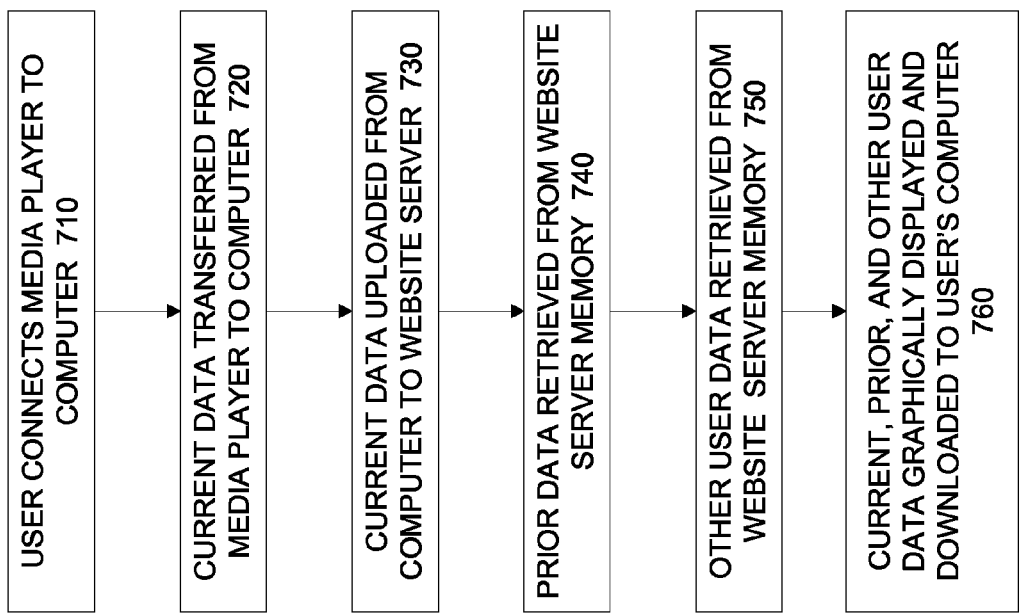

FIG. 7A illustrates a method of using a third-party website to display workout data according to an embodiment of the present invention. In this method, the user connects a media player to her computer. Data is transferred from the media player to the computer, then uploaded to a website server. Other data is combined with this and graphically displayed on the user's computer.

Specifically, in act 710, a user connects the media player to her computer. In act 720, current data is transferred from the media player to the computer. This workout data is uploaded from the computer to a third-party website server in act 730. Other data, such as prior workout data or other user data may also be retrieved from server memory in acts 740 and 750. This data is then graphically displayed on the user's computer in act 760.

In these examples, data is written to a media player during a workout. Later, the data is transferred to a computer. In other embodiments of the present invention, data can be written directly to a computer or third party website. This may be accomplished using a web-enabled media player. For example, data may be written to the media player, then uploaded over a wireless network or cellular network to a computer or third-party server.

In these examples, data is written by the sports equipment to the media player. Data on the media player is uploaded to the user's computer. The user's computer can then pass the data on to a third-party website and the third-party website can then display this and other data on the user's computer. In other embodiments of the present invention, other data flows are possible.

For example, a user may use her computer to log on to the third-party website. User information, such as a user identification or nickname, may be provided by the user to the website. The website can then provide this data to the media player via the user's computer. The media player can in turn provide this data to the sports or other equipment when communication is established between the media player and the equipment. These acts are shown further in the following figure.

FIG. 7B illustrates a method of transferring data from a user's computer to sports equipment via a website according to an embodiment of the present invention. In this method, a user enters data on a computer. This data may be an identification, nickname, or other type of data. This data is uploaded to a third-party website server. The third-party website server then transfers this data to the media player via the computer. The data is then transferred to the sports equipment.

Specifically, in act 770, a user enters data on a website using her computer. In act 775, the data is transferred from the website to the user's computer. In act 780, the data is transferred from the computer to a media player. In act 785, a communication link is established between the sports equipment and the media player. In act 790, the data is transferred from the media player to the sports equipment.

When a user uses a media player in conjunction with a piece of sports or other equipment, it is desirable that the equipment provides information back to the user as well as record workout data. Flowcharts illustrating methods of performing these tasks are shown in the following three figures.

Figure 8:
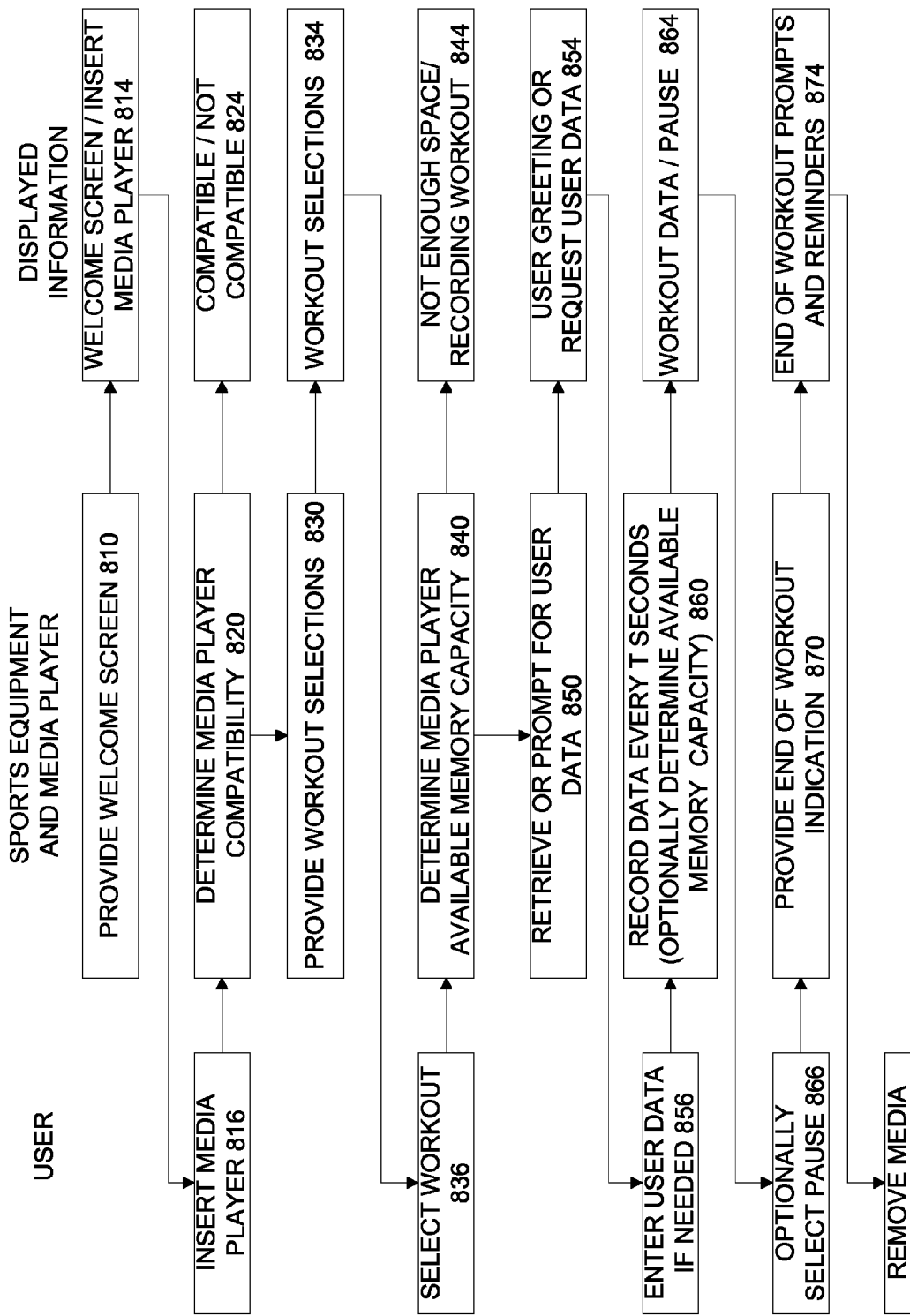
FIG. 8 illustrates the activities performed by sports equipment and a media player during a workout session according to an embodiment of the present invention.

FIG. 8 illustrates the activities performed by sports equipment during a workout session according to an embodiment of the present invention. In this embodiment of the present invention, the sports equipment writes workout data onto the media player. Also, the sports equipment or media player, or combination of the equipment and media player, provides various prompts at different times during the workout session. These prompts may be shown using a display on the sports equipment, on the media player, or these displays may work in conjunction with each other.

Specifically, in act 810, the sports equipment provides a welcome screen. At this time, the information displayed is a welcome screen, which may inform a user the way to establish communication between a media player and the sports equipment. In act 816, a user inserts a media player into the sports equipment or otherwise establishes communication between the media player and the sports equipment.

In act 820, the capabilities of the media player can be determined. Information regarding the compatibility or incompatibility of the media player may be displayed in act 824. In act 830, a selection of workouts may be provided and displayed in act 834. The user may select one of these workouts in 836.

Once the workout is selected, the media player may determine whether the media player has enough capacity to store information for this workout in act 840. If there is enough room, an indication that there is enough memory space and that data will be recorded may be provided in act 844. If there is not enough memory space, this may be indicated in act 844. This information may be handled differently in various embodiments of the present invention. For example, if the chosen workout is 1 hour, the media player can determine how much memory will be required since data will be recorded every T seconds, as outlined below. If there is enough space, that can be communicated to the user. If there is not enough space, that can be communicated. However, in some embodiments of the present invention, the duration of a selected workout may be undetermined. In this case, the media player may inform the user that it has room for a workout of duration X. In some embodiments of the present invention, X is provided to the user only when it is below a threshold; it may not be of interest to a user that a workout of 28 hours can be recorded.

At this point, or at another point, user data may be prompted for or retrieved. This may be in the form of the user greeting or request for user data in act 854. If needed, the user can enter this data in act 856. This data may be entered using an interface on the sports equipment, media player, or both. Again, this may be as simple as identifying oneself from a list of users. Alternatively, no identification may be needed. As the workout is occurring, data is recorded every T seconds in act 860. This limits the data loss if communication between the media player and the sports equipment is terminated, as for example, when a user removes the media player. Also at this time, the media player may optionally determine how much memory capacity it has left. From this, it can let the use know how much longer it can record workout data. This information along with workout data or information regarding the workout data may be provided on the display in act 864. This information or data may include calories burned, elapsed time, distance, speed, heart rate, incline, resistance, effort, and other types of information. An option to pause may also be displayed. This pause may be optionally selected in act 866. The use of this pause function avoids having the sports equipment write large amounts of empty data to the media player.

At the end of the workout, an end of workout indication may be provided to the user in act 870. This may be displayed in act 874. This indication may include congratulatory statements, reminders to resynchronize the media player, or other such information. In act 876, the user may remove the media player.

Figure 9:
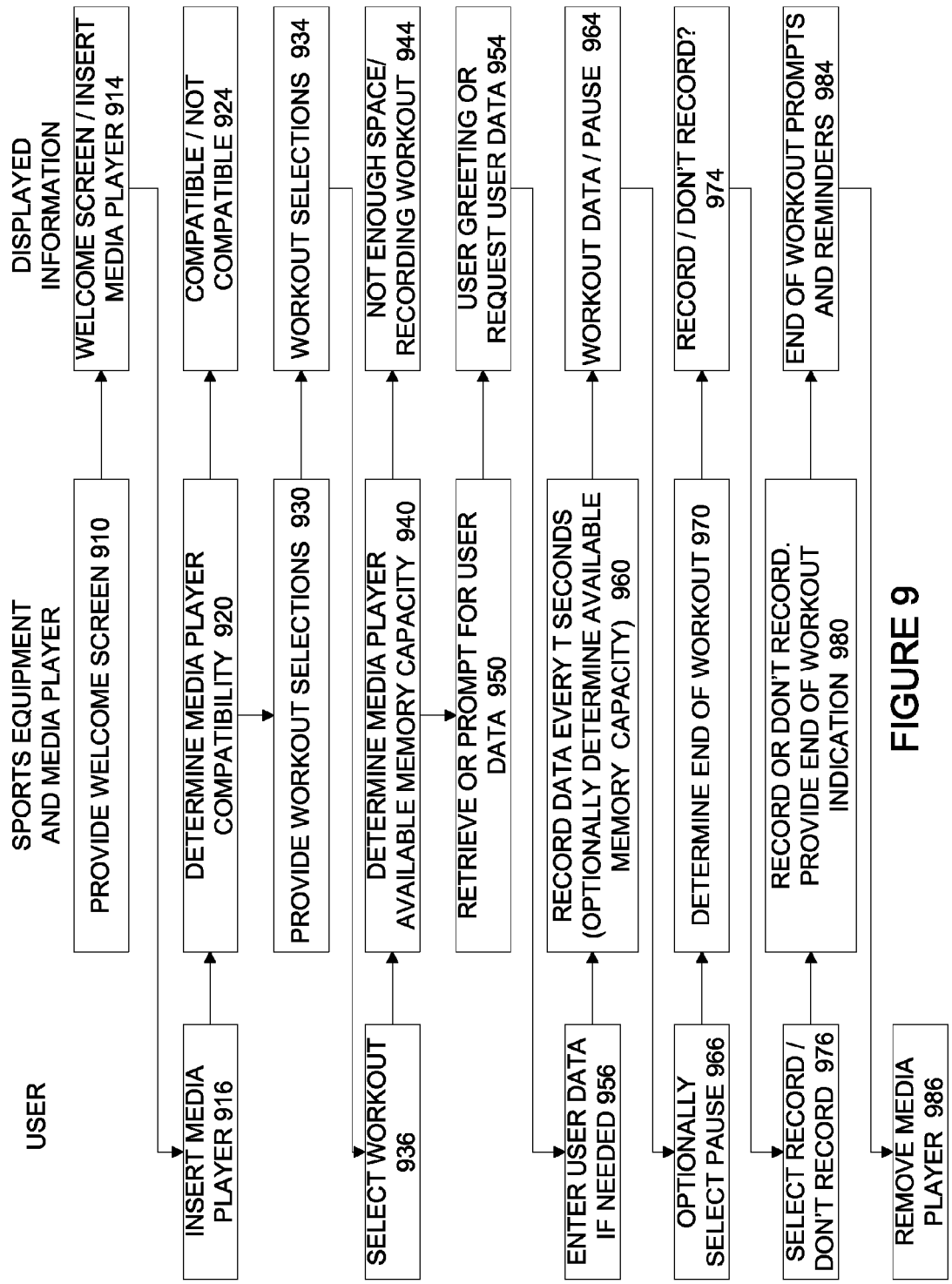
FIG. 9 illustrates another method of collecting data and providing prompts during a workout session according to an embodiment of the present invention.

FIG. 9 illustrates another method of collecting data and providing prompts during a workout session according to an embodiment of the present invention. In this method, the option of recording or not recording the data is provided to the user at the end of the workout.

Specifically, in act 970, the end of the workout is determined. In act 974, the option to record or not record the data is provided. The user may select one of these options in act 976. If the selection is made to not record, the data is not recorded. If the selection is made to record the data, the data is recorded in act 980. In either case, an end of workout indication may be provided in act 984. Specifically, workout prompts and reminders may be provided in act 984. The media player may be removed in act 986.

Again, a user may end a workout session early by removing the media player or otherwise breaking a communication link between the media player and sports equipment. This is shown in the following figure.

Figure 10:
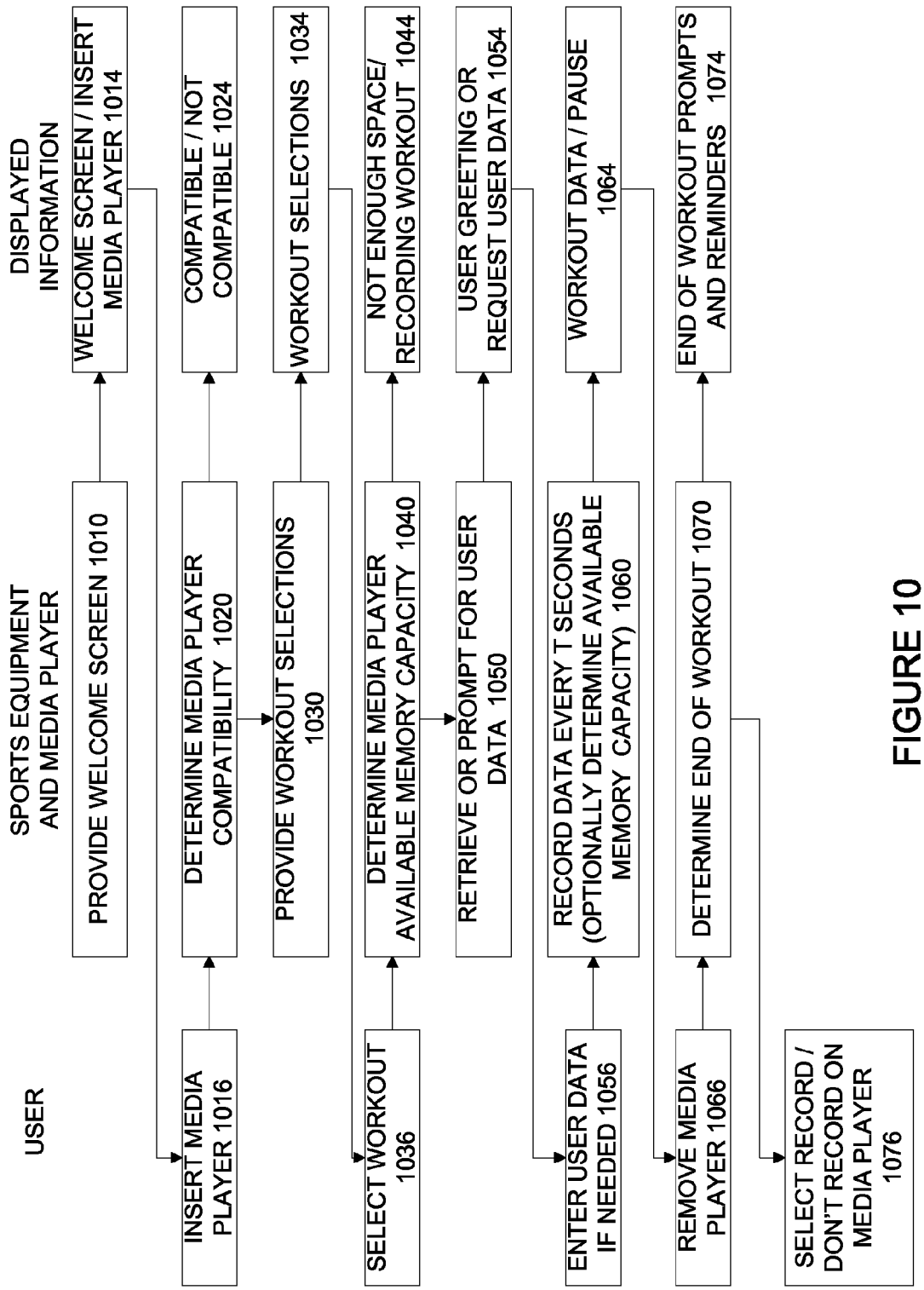
FIG. 10 illustrates the activities performed by sports equipment and a media player when a user removes a media player or otherwise breaks a communication link between a media player and sports equipment before the expected end of a workout session according to an embodiment of the present invention.

FIG. 10 illustrates the activities performed by sports equipment when a user removes a media player or otherwise breaks a communication link between a media player and sports equipment before the expected end of a workout session according to an embodiment of the present invention. Specifically, in act 1066, the media player is removed by the user at a time before the time the sports equipment expects the workout session to end. This triggers an end of workout determination by the sports equipment in act 1070. End of workout prompts and reminders may be displayed in act 1074. The user may further be asked whether she wants to record or not record data on the media player in act 1076. It the option to not record is selected, the data can be deleted from the media player. If the option to record is selected, the data is retained on the media player for uploading to the user's computer at a later time.

New types of media players and related devices are consistently being provided to the marketplace. Each successive generation of these devices has various capabilities. Moreover, different firmware or software releases may mean that different devices within a particular device type also have different capabilities. In some embodiments of the present invention, it may be beneficial if the sports or other equipment can utilize various capabilities of the media player to the extent that they are available. However, when these capabilities are not available, it is desirable that the sports equipment continue proper operation in their absence. Accordingly, it is desirable that the sports equipment be able to accurately assess the capabilities of the media player. A flowchart illustrating one method of performing this is shown in the following figure.

Figure 11:
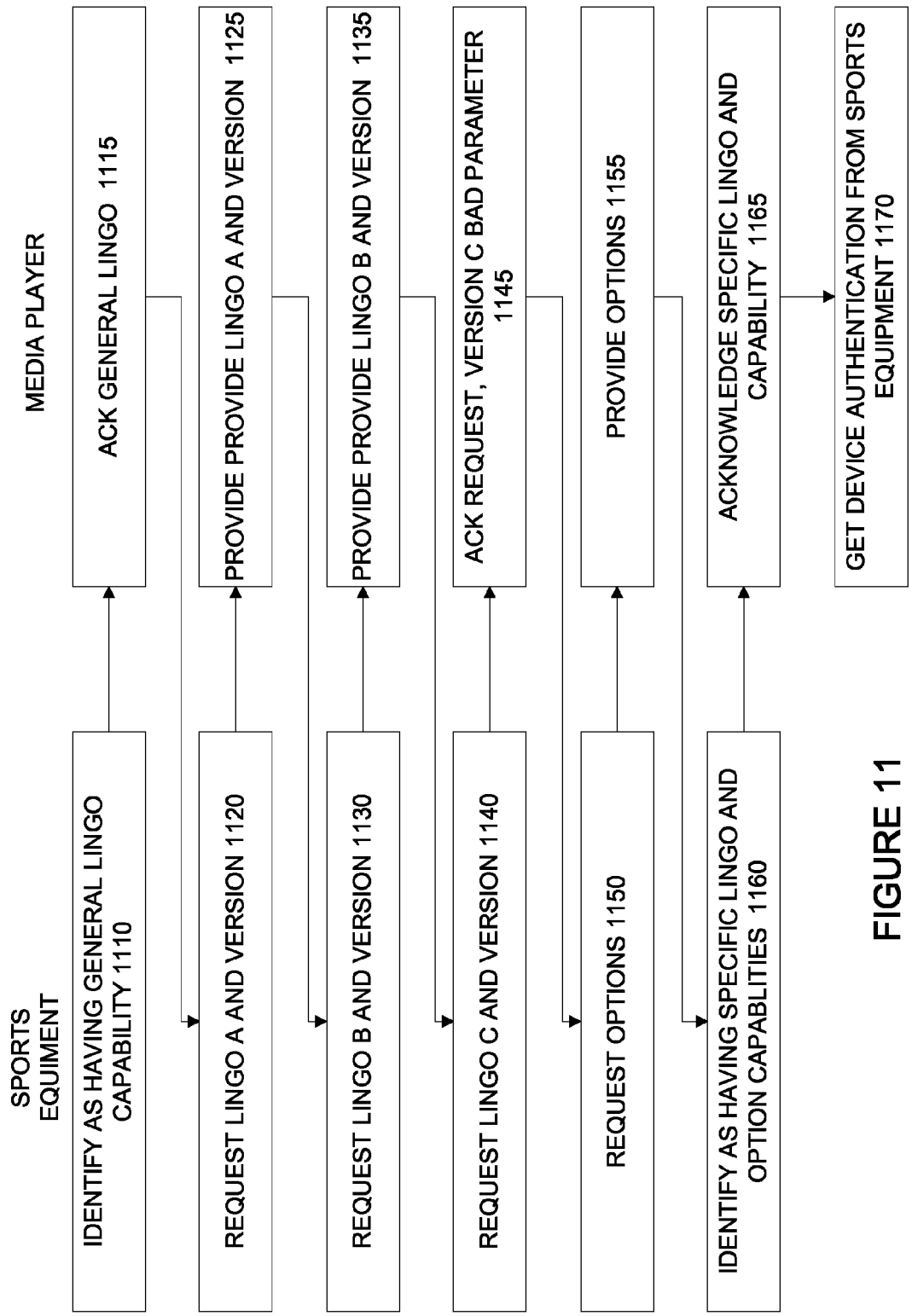
FIG. 11 illustrates a method that may be used by sports equipment to assess the capabilities of the media player according to an embodiment of the present invention.

FIG. 11 illustrates a method that may be used by sports equipment to assess the capabilities of the media player according to an embodiment of the present invention. This interrogative process avoids a situation where an error condition arises when an item of sports equipment identifies itself as communicating using a lingo not understood by the media player.

Specifically, in act 1110, the sports equipment identifies itself as being capable of communications using a general lingo. The media player acknowledges this in act 11 15. In act 1120, the sports equipment requests information regarding a particular lingo and version from the media player. In this example, the media player is capable of understanding this lingo and replies appropriately in act 1125. In act 1130, the sports equipment requests information regarding another lingo and version from the media player in act 1130. Again, the media player is capable and replies appropriately in act 1135. A further request for information regarding another lingo and version is made to the media player in act 1140. In this case, the media player is not capable of understanding this lingo. Accordingly, the media player acknowledges the requests and sends back a bad parameter response in act 1145. The sports equipment requests options that the media player may have in act 1150. This information is provided by the media player in act 1155. In act 1160, the sports equipment identifies itself as having the specific lingo and option capabilities determined by the above interrogatory. The media player acknowledges this in act 1165. In act 1170, the media player may retrieve device authentication from the sports equipment.

Various types of data may be written to the media player memory before, during, and after a workout session. Examples of data that may be written are shown the following figure.

FIG. 12 illustrates data that may be written to a media device memory by sports equipment before, during, and after a workout session according to an embodiment of the present invention. For each piece of data, the memory space allocated for the data is also shown in parentheses. In this example, data is written using XML format, though in other embodiments of the present invention, other data formats may be used. Identifying information is provided at the beginning and end of the complete data package. Similarly, identifying information is included at the beginning and end of each particular information type.

Specifically, identification data identifying this as gym data is provided as data 1200 and 1295. Gym equipment information 1220 is also included. This includes manufacturer ID, manufacturer name, equipment type, model, serial number, as well as the name and location of the gym. User information 1230, which may include user profile information such as name, weight, gender, or other information, may also be included.

Workout data includes a workout template 1240, interval data 1250, and workout summary 1270. Workout template data 1240 may include such information as a workout name, caloric goal, time goal, distance goal, speed goal, and heart rate goal.

Interval data 1250 is data that is written to the media player periodically, for example every 10 or 20 seconds. This data can include current calories, current elapsed time, current distance, current speed, current heart rate, incline, and resistance/effort information. This data can be combined in a workout summary 1270, which may include total calories, total elapsed time, total distance, and average speed.

Once the workout is done and the media player is removed from the sports equipment, or the communication link between the sports equipment and media player is otherwise interrupted, end of file data such as a signature 1290 may be written by the media player. In various embodiments of the present invention, files are signed or verified. This signing or verification requires an increase in the file size that is written to the media player. In a specific embodiment of the present invention, this signing doubles the file size written to the media player. Also, end of file data such as media player information including start and end times, model, software version, and serial number may be written.

Typically, equipment, user, and workout template information may be written to the media player before the workout begins. Interval data can be written during the workout session. End of file data such as a workout summary and signature data can be written after the workout, either by the sports equipment or the media player itself. The media player information can be written after the workout, though most data, except for end time, can be written some time before the end of the workout.

Again, in various embodiments of the present invention, it is desirable to provide data from other users. This data is useful for competitions as a way of encouraging progress by the user. This data may be collected ahead of time, or it may be collected in real-time. Examples of real-time data collection and sharing are shown in the following figures.

FIG. 13 illustrates a system including two items of sports equipment that may be used for real-time competitions. In this example, treadmills are depicted, though as before, other types of sports or other equipment may be used. Each treadmill is in communication with a media player. Specifically, treadmill 1 is in communication with media player 1, while treadmill 2 is in communication with media player 2. These treadmills may be located in the same building, or they may be located in different buildings, in different cities, or even in different continents. In this example, media on one media player can be shared between the two treadmills. Also, data from both treadmills can be displayed on each treadmill, thus showing the users their respective standings in the competition.

Information may be shared between the sports or other equipment using a communication link through the equipment itself, through the media players, or through a combination of equipment and media players. For example, the sports equipment may include or be associated with optical, wired, or wireless communication circuits that can form a communication link via the Internet, WiFi, LAN, Bluetooth, one of the IEEE802.11 standards, or other network or a combination of these. Also, information may be shared between the sports or other equipment using a communication link between the media players. For example, the media players may include wireless circuitry for WiFi, Bluetooth, cellular, Internet, LAN, one or more of the IEEE 802.11 standards, or other networks. The media players may communicate over short distances using, for example, Bluetooth, one or more of the IEEE 802.11 standards, or other wireless, optical, or wired connections. The media players may also communicate with each other over long distances, for example using the Internet, cellular, or other connection. Information may also be shared in other ways, for example, media on a media player may be shard between the media player and a piece of sports equipment located remotely from the media player using any of the above or other networks. Also, while two pieces of sports equipment are shown in this example, this concept may be extended to any number of pieces of sports equipment and media players. The activities performed by the two items of sports equipment are shown in the following figures.

Figure 14:
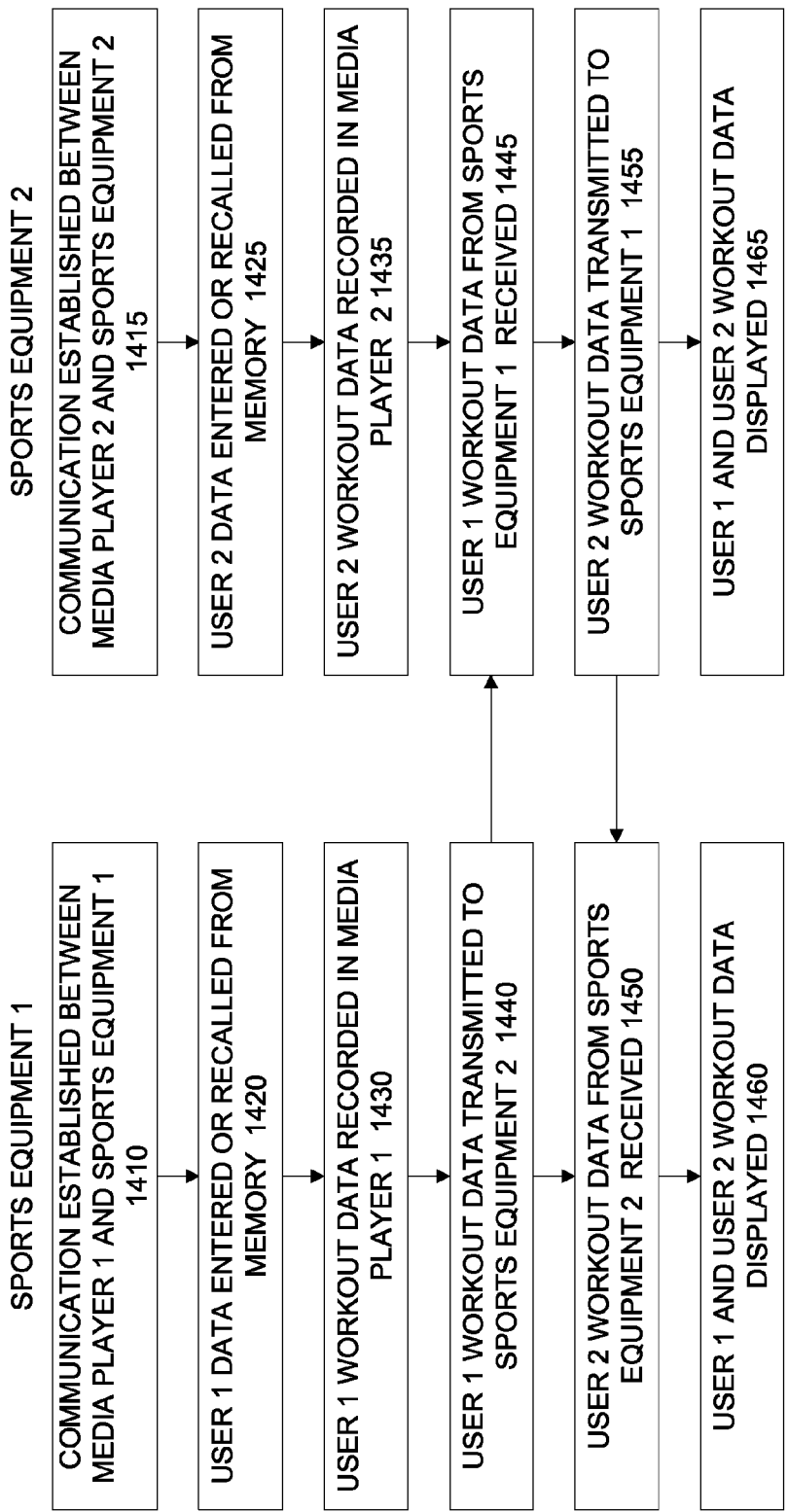
FIG. 14 illustrates the activities performed by two items of sports equipment during a real-time competition according to an embodiment of the present invention.

FIG. 14 illustrates the activities performed by two items of sports equipment during a real-time competition according to an embodiment of the present invention. Communication is established between a first media player and first sports equipment in act 1410. Similarly, communication is established between a second media player and second piece of sports equipment in act 1415. In act 1420 and 1425, user data is entered or recalled from memory. A workout data is recorded on the media players in act 1430 and 1435. User 1 workout data is transmitted to the second sports equipment in act 1440. In act 1445, user 1 workout data is received from sports equipment 1 by sports equipment 2. In act 1455, workout data is transmitted to sports equipment 1 from sports equipment 2. In act 1450, this data is received from sports equipment 2. User 1 and user 2 workout data is displayed in acts 1460 and 1465.

Again, in various embodiments of the present invention, it is desirable to share media between two or more users. An example of this is shown in the following figure.

Figure 15:
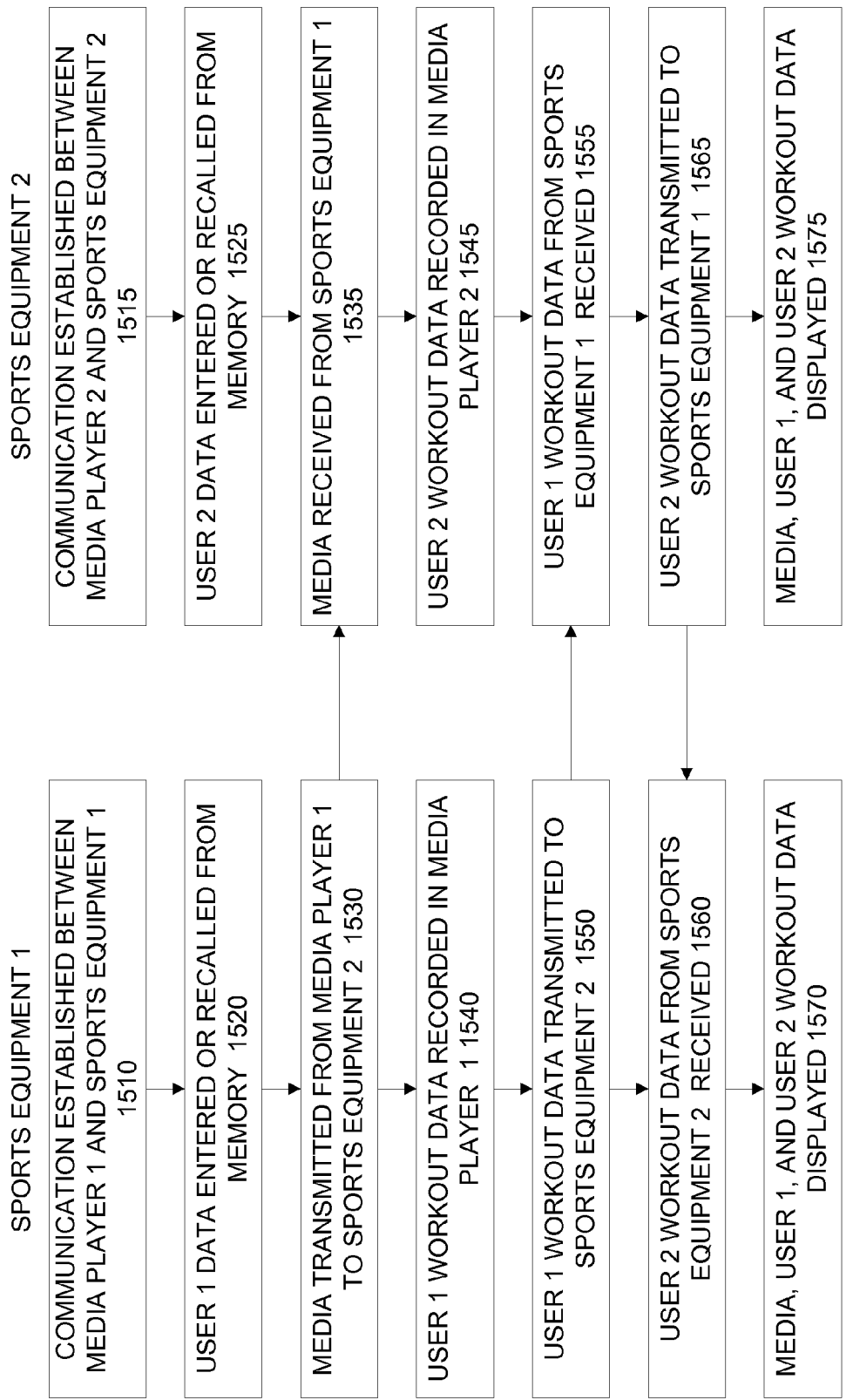
FIG. 15 illustrates activities performed by two items of sports equipment during a real-time competition where media is shared according to an embodiment of the present invention.

FIG. 15 illustrates activities performed by two items of sports equipment during a real-time competition where media is shared according to an embodiment of the present invention. As before, communication is established between the media players and sports equipment in act 1510 and 1515. User data is entered or recalled from memory in acts 1520 and 1525. In this example, media is transferred from media player 1 to sports equipment 2 in act 1530. The media is received from the sports equipment 1 in act 1535 and provided to the user. Workout data is recorded in acts 1540 and 1545. Workout data is transferred between the sports equipment in act 1550, 1555, 1560, and 1565. The media, user 1, and user 2 data is displayed or otherwise provided to the users in acts 1570 and 1575.

In these examples, workout data may be transmitted from a first item of sports equipment to a second in a number of ways. For example, workout data may be transmitted from the first item of sports equipment to the second directly, that is, without involving the media players. Also, data may be generated by the first item of sports equipment then transferred to its associated first media player, which then transmits the data to the second item of sports equipment. The data may be received by the second item of sports equipment either directly or via its associated second media player. To achieve this, either or both sports equipment and media players may include or be associated with circuitry for wireless, wired, or optical communications. These may include one or more of the IEEE 802.11 standards, WiFi, Bluetooth, LAN, cellular, Internet, or other types of network communications or combination of these.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

What is claimed is:

1. A method of providing competitive workout data comprising, with a first item of sports equipment:
    establishing a first communication link with a first media player;
    receiving media from the first media player through the first communication link;
    providing the media to a user;
    receiving user profile data from the media player;
    generating first workout data, wherein the first workout data depends at least in part on the user profile data;
    writing the first workout data to the first media player;
    receiving second workout data directly from a second item of sports equipment; and
    displaying information based on the first workout data and the second workout data.

2. The method of claim 1 further comprising receiving control information from a user that controls the media from the first media player.

3. The method of claim 1 further comprising providing media to the user through a headphone jack, speakers, or a display.

4. The method of claim 1 wherein the first item of sports equipment is a treadmill.

5. The method according to claim 1 where the second workout data is received from the second item of sports equipment prior to receiving the first workout data.

6. The method according to claim 1 where the second workout data is received from the second item of sports equipment contemporaneously with receiving the first workout data.

7. The method according to claim 1 further comprising writing the second workout data to the first media player.

8. A method of providing competitive workout data comprising, with a first portable media player:
    establishing a first communication link with a first item of sports equipment;
    providing media to the item of sports equipment;
    providing user profile data to the item of sports equipment;
    receiving first workout data from the first item of sports equipment, wherein the first workout data depends at least in part on the user profile data;
    storing the first workout data;
    receiving second workout data from a second portable media player; and
    providing the second workout data to the first item of sports equipment.

9. The method of claim 8 wherein the media comprises either or both of music and video.

10. The method of claim 8 wherein the second workout data is generated substantially contemporaneously by a second item of sports equipment.

11. The method of claim 8 further comprising receiving media control data from the first item of sports equipment.

12. The method of claim 8 wherein the second workout data is received from the second portable media player contemporaneously with the first workout data.

13. The method of claim 8 wherein the second workout data is received from the second portable media player prior to receiving the first workout data.

* * * * *